United States Patent
Vernice et al.

(10) Patent No.: US 6,348,199 B1
(45) Date of Patent: Feb. 19, 2002

(54) SKIN TREATMENT CREAM

(76) Inventors: Joseph Vernice, 80 Parkview Dr., W., Shirley, NY (US) 11967; Alfred R. Globus, 26-53 210th St., Bayside, NY (US) 11360

(*) Notice: Subject to any disclaimer, the term of this patent is extended or adjusted under 35 U.S.C. 154(b) by 0 days.

(21) Appl. No.: 08/177,576

(22) Filed: Jan. 5, 1994

Related U.S. Application Data

(63) Continuation-in-part of application No. 08/036,374, filed on Mar. 24, 1993, now abandoned.

(51) Int. Cl.[7] ................................. A61K 7/48
(52) U.S. Cl. .................. 424/401; 424/78.02; 514/786; 514/788; 514/937; 514/946; 514/947
(58) Field of Search .............................. 424/401, 78.02; 514/772.4, 786, 788, 937, 946, 947

(56) References Cited

U.S. PATENT DOCUMENTS 4,837,019 A * 6/1989 Georgalas et al. .......... 424/401
5,288,493 A * 2/1994 Martino et al. ............. 424/401

* cited by examiner

*Primary Examiner*—Jyothsna Venkat
(74) *Attorney, Agent, or Firm*—Evelyn M. Sommer

(57) ABSTRACT

A clear, transparent highly stable skin moisturizing and lubricating composition is provided comprising the product obtained by combining polyglyceryl methacrylate with a pharmaceutically acceptable silicone, in the presence of a suitable emulsifier under application of pressure in the range of about 13,000 to about 50,000 psi. The compositions are adapted for use as cosmetics and/or carriers for active drugs and serve in this form for treatment of skin irritations, burns, skin infections and the like. A method of preparing the compositions of the invention is disclosed. The invention also contemplates methods for lubricating and moisture replenishment of the skin, treating burns, skin infections and the like by topically applying the disclosed skin treatment compositions of the invention.

13 Claims, No Drawings

SKIN TREATMENT CREAM

This application is a continuation-in-part of application Ser. No. 08/036,374 filed Mar. 24, 1993 and now abandoned.

The present invention relates to improved skin moisturizing and lubricating compositions which are additionally adapted for serving as carriers for pharmaceutically active agents in which form they are useful in the treatment of skin irritations, burns or infections. More particularly, this invention relates to optically clear, transparent, highly stable moisturizing and lubricating compositions having the additional utility aforenoted.

Oil free, non-greasy skin treatment compositions for counteracting moisture loss and promoting healing of the skin, as for example, burned or sun-burned skin are known. In U.S. Pat. No. 4,837,019, compositions for counteracting moisture loss and promoting the healing of burned skin are described which include as the moisturizing and/or healing agent a component formed of polyglyceryl methacrylate, glycerine, allantoin, panthenol, amino acid complex, and fibronectin. The component aforedescribed is present in an amount of a 2–30% of the total composition, the make up of the remainder of the composition being dependent on whether the composition is in the form of an emulsion, cream, gel, aqueous/alcoholic or glycol solution or microemulsion.

The compositions of U.S. Pat. No. 4,837,019 have been found not to be stable undergoing phase separation on storage. In accordance with U.S. Pat. No. 4,863,725, moisturizing compositions are provided which are clear, oil-free and therefore non-greasy to the skin and touch which include as the major moisturizing component a composition derived from glycerol and acrylic or methacrylic polymers (polyglyceryl methacrylate), one or more skin feel enhancers which is preferably a polyol, one or more preservatives, and water as a carrier. The moisturizer composition also preferably includes one or more thickeners, one or more skin conditioning agents, one or more astringents and/or colorants and/or fragrances. The aforesaid moisturizing compositions may be in the form of clear lotions or gels.

In accordance with the present invention, an improved skin moisturizing and lubricating composition is provided which is a clear transparent, highly stable composition in gel form which comprises the product obtained by combining polyglyceryl methacrylate with a pharmaceutically acceptable silicone under condition of elevated pressure falling within the range of about 13,000 to 50,000 psi in the presence of a suitable emulsifier.

The polyglyceryl methacrylate employed contains approximately 50% water, is in the form of a white transparent gel and may or may not contain incidental ingredients, such as propylene glycol which may be present in an amount of 2% or less. A preferred polyglyceryl methacrylate is Lubrajel CG, a registered trademark of United Guardian Inc., which is distributed by Meadow Technical Corp., Livingston, N.J. The preferred form of Lubrajel has a viscosity at 20° C. (Brookfield RTV) ranging from about 400,000 to about 5,000,000, a specific gravity of 1.2 mg/ml, is completely soluble in water and is substantially stable at 250° F., even after sealed storage for 3 years at 20° C. Lubrajel CG is a clathrate formed by the reaction of glycerin and methylmethacrylate.

The polyglyceryl methacrylate is combined with the silicone in an amount of 1–10% and preferably 1–5%.

The silicone employed for combination with the polyglyceryl methacrylate may be cyclomethicone and/or dimethiconol and/or dimethicone copolyols of varying molecular weight. Dimethicone copolyol is a copolymer of dimethlsiloxane and polyethylene oxide or propylene oxide.

Suitable emulsifiers include polyethylene glycol 20 sorbitan monolaurate (Polysorbate 20), polyethylene glycol 5 soya sterol, sorbitan tristearate, sorbitan trioleate, glyceryl, monopalmitate, diethanolamine cetyl phosphate, glyceryl monopalmitate, glyceryl monostearate, polyethylene glycol 100 stearate, polyethylene glycol 20 stearyl ether (Brij 78, Steareth 20), polyethylene glycol ether of lauryl alcohol (Laureth 23), polysorbate 80 (Tween 80), lecithin, etc. The emulsifier may constitute a single emulsifier or a mixture of two or more of these emulsifiers or others which are approved for cosmetic use.

The emulsifier is employed in approximately the same amount as the silicone i.e., 1–10% and preferably 1–5%.

The composition of the invention is recovered as a clear, transparent, hydrophilic gel. No separate gelling agents are required for its formation.

The polyglyceryl methacrylate containing about 50% water will be present in the composition of the invention in an amount of 80– 98% preferably 90–98%.

The skin treatment compositions of the invention are prepared by the steps of mixing the polyglyceryl methacrylate, silicone and emulsifiers to form, a uniform, homogeneous mixture and then applying pressure in the range of about 13,000 to 50,000 psi forming a stable microemulsion.

The microemulsion produced following such compression when subjected to high speed centrifuging for two or more hours does not show any evidence of separation.

The invention additionally provides a method for treating skin for replenishing moisture in the skin which includes the step of applying to the skin a composition in accordance with the invention one or more times a day.

If the composition is intended for use to promote the healing of burned skin or to treat irritated or infected skin, the composition will have had incorporated therein an effective amount of panthenol (d- or dl-), fibronectin, allantoin, amino acid complex, etc.

The composition of the invention i.e., polyglyceryl methacrylate:silicone has been found to possess layering properties lending itself to formulation as a medical device particularly adapted for use as a carrier for various treatment agents such as: phenols, urea, aloe vera, etc.

Examples of preferred formulations in accordance with the invention include but are not limited to the following:

| Ingredient | Per Cent |
|---|---|
| I Polyglyceryl methacrylate (60% bound water) | 95% |
| Cyclomethicone (silicone) | 3% |
| Polysorbate 20 (emulsifying agent) | 2% |
| II Polyglyceryl methacrylate (50% bound water) | 98% |
| Dimethiconol (silicone) | 1% |
| Sorbitan tristearate (emulsifying agent) | 1% |
| III Polyglyceryl methacrylate (45% bound water) | 92% |
| Cyclomethicone + Dimethiconol (silicone) | 5% |
| Polysorbate 80 (emulsifying agent) | 3% |
| IV Polyglyceryl methacrylate | 97.3% |

-continued

| Ingredient | Per Cent |
|---|---|
| (55% bound water) | |
| Dimethicone copolyol (silicone) | 1% |
| Laureth 23 (emulsifier) | 0.7% |
| Panthenol (healing agent burns) | 1% |
| V Polyglyceryl methacrylate (60% bound water) | 96.6% |
| Cyclomethicone and Dimethiconol (silicones) | 1.5% |
| Polysorbate 20 (emulsifier) | 1.4% |
| Fibronectin (wound healing) | 0.5% |

A skin treatment agent corresponding to Formulation 1 above, was prepared by mixing the polyglyceryl methacrylate with the silicone and the emulsifier in a lightning mixer for 2 hours for a time sufficient to form a homogeneous mixture. The resulting mixture was introduced into a super-micro emulsifier and subjected to a pressure of about 17,500 psi to form a clear transparent stable gel form microemulsion i.e., a microemulsion of polyglyceryl methacrylate:silicone. These microemulsions are then suitably packaged, for example in jars, pails or drums.

The gel composition of the invention, formulated as above set out are stable over prolonged periods of time. Examination of the gel composition after 2 years shows no signs of instability whatsoever.

If it is attempted to dilute the gel formulations by addition of water thereto, hazing of the gel takes place i.e., the formulation is no longer clear. The addition of further quantities of an emulsifier as for instance, ethoxysorbitan laurate does not result in a reversion i.e., return to the original clarity. This is also true when additions of propylene glycol or hexyleneglycol are made. However, it has been found that the addition of further quantities of polyglyceryl methacrylate tends to restore the original clarity, probably due to the increase in the number of hydroxy groups present.

Based on the known freedom from toxicity of each component it can be assumed that the finished product is also non-toxic. When the composition was applied to the skin of human subjects no irritation was observed.

The compositions of the invention may be formulated to produce a wide range of cosmetic products such as skin moisturizers, lubricants and conditioners; also hair-care products, shaving lotions, etc. Formulations for carrying various active agents may be produced with these compositions.

When used as a carrier for a pharmaceutical agent, the skin treatment compositions of the invention may include phenols, urea, aloe vera, allantoin, amino acids, fibronectin and the like depending on the purpose of application.

When used as a moisturizing composition approximately 1.0 ml of the polyceryl methacrylate:silicone composition is applied in a routine manner once to three times daily to the desired area for treatment.

If the application is for medical treatment (anti-inflammatory, anti-infective, burn therapy etc.), the nature of the treatment, the degree and extent of therapy indicated will result in the selection of an at least a therapeutically effective amount of the active agent for topical application to the skin.

What is claimed is:

1. A clear, transparent, highly stable skin treatment composition in gel form for replenishing moisture in the skin and promoting healing of burned, infected, and irritated skin, comprising the product produced by combining 80–98% by wt. polyglyceryl methacrylate containing about 50% water, with about 1–10% by wt. of a silicone in the presence of about 1–10% by wt. of a silicone which is a member selected from the group consisting of cyclomethicone, dimethiconol, dimethicone copolyols and mixtures of cyclomethicone and dimethiconol and dimethicone co-polymers thereof in the presence of 1–10% by wt. of an emulsifier under conditions of elevated pressure ranging from about 13,000 to about 50,000 psi.

2. The composition as defined in claim 1 comprising polyglyceryl methacrylate: silicone wherein silicone designates a member selected from the group consisting of cyclomethicone, dimethicone, mixtures of cyclomethicone and dimethiconol and dimethicone copolymers.

3. The composition as defined in claim 1 wherein said emulsifier is a member selected from the group consisting of polyethylene glycol 20 sorbitan monolaurate, polyethylene glycol 5 soya sterol, sorbitan tristearate, sorbitan trioleate, glyceryl monopalmitate, diethanolamine cetyl phosphate, glyceryl monopalmitate, glyceryl monostearate, polyethlene glycol 100 stearate, polyethylene glycol ether of lauryl alcohol, polysorbate 80, and lecithin.

4. The composition as defined in claim 1 wherein there is additionally present a pharmaceutically active agent.

5. The composition as defined in claim 4 wherein said pharmaceutically active agent is a member selected from the group consisting of phenol, urea, allantoin, fibronectin, amino acids, panthenol and mixtures thereof.

6. A method of preparing the composition as defined in claim 1 which comprises the steps of forming a uniform, homogenous mixture of 80–98% by wt. polyglyceryl methacrylate, containing about 50% water, with about 1–10% by wt. of a silicone which is a member selected from the group consisting of cyclomethicone, dimethiconol, dimethicone copolyols and mixtures of cyclomethicone and dimethiconol and dimethicone co-polymers thereof and about 1–10% by wt. of an emulsifier, subjecting the resulting mixture to a pressure of about 13,000 to about 50,000 psi. for a time sufficient to form a microemulsion of the polyglyceryl methacrylate:silicone.

7. A method according to claim 6 wherein there is additionally present a pharmaceutically active agent.

8. A method of providing moisture to alleviate dry skin conditions which comprises topically applying to the skin of a subject an effective amount of a composition according to claim 1.

9. A method of promoting healing of irritated skin which comprises topically applying to the skin of a subject an effective amount of a composition according to claim 4.

10. A method of treating burned skin which comprises topically applying to the skin of a subject an effective amount of a composition according to claim 4.

11. A method of treating infected skin which comprises applying to the skin of a subject an effective amount of a composition according to claim 4.

12. The composition as defined in claim 1 wherein said polyglyceryl methacrylate is present in an amount of about 90 to 98% by wt.

13. A method according to claim 6 wherein said polyglyceryl methacrylate is present in an amount of about 90 to 98% by wt.

* * * * *